United States Patent [19]

Lewis

[11] Patent Number: 4,935,428

[45] Date of Patent: Jun. 19, 1990

[54] TREATING OPIATE DEPENDENCE

[75] Inventor: John W. Lewis, North Humberside, United Kingdom

[73] Assignee: Reckitt & Colman Products Limited, London, England

[21] Appl. No.: 276,400

[22] Filed: Nov. 25, 1988

[30] Foreign Application Priority Data

Dec. 3, 1987 [GB] United Kingdom ............... 8728294

[51] Int. Cl.⁵ ............................................. A61K 31/44
[52] U.S. Cl. ..................................... 514/282; 514/812
[58] Field of Search ................................ 514/282, 812

[56] References Cited

U.S. PATENT DOCUMENTS 4,661,492  4/1987  Lewis et al. ..................... 514/282

Primary Examiner—Stanley J. Friedman
Attorney, Agent, or Firm—Bacon & Thomas

[57] ABSTRACT

A pharmaceutical composition in sublingual unit dosage form for maintenance treatment of opiate addicts comprising from 2 to 8 mg buprenorphine and an amount of naltrexone sufficient to substantially attenuate the euphorigenic effect of the buprenorphine when injected and to provide greater opiate blocking effect than that of naltrexone alone.

7 Claims, No Drawings

TREATING OPIATE DEPENDENCE

This invention relates to compositions useful for the treatment of opiate dependence and more particularly to compositions containing naltrexone and buprenorphine.

Naltrexone (INN for 1-N-cyclopropylmethyl-14-hydroxynordihydromorphinone) is a pure opiate antagonist which, when administered orally (50 mg/day) as a maintenance drug for opiate addicts, blocks the effects of self-administered opiates and this contributes to the extinction of drug craving. Unfortunately, only about 10 percent of addicts inducted on to a naltrexone treatment regime remain in treatment since naltrexone has no positive reinforcing effect to satisfy the needs of the addict. It also has the disadvantage that it precipitates abstinence in opiate abusers including those with only a low level of physical dependence. Thus an addict must be detoxified and be drug free for at least ten days before starting naltrexone treatment.

Buprenorphine (INN for N-cyclopropylmethyl-7&-[1-(S)-hydroxy-1,2,2-trimethylpropyl]6,14-endoethano-6,7,8,14-tetrahydronororipavine) has been shown in man to be a potent antagonist analgesic lacking the psychotomimetic effects found with other antagonist analgesics. Buprenorphine effectively relieves moderate to severe pain in doses of 0.1 mg or more administered either parenterally or sublingually. The optimum therapeutic range for single doses is 0.3 mg–0.6 mg by injection and 0.1 mg–0.4 mg for sublingual tablets. In animal tests and in man buprenorphine has been shown to have both agonist (morphine-like) and (morphine) antagonist properties. However from direct dependence studies in animals and in man it has been concluded that buprenorphine does not produce significant physical dependence and the potential to produce psychological dependence is low as indicated by animal self administration studies and by the measurement of euphorigenic effects in human post addicts. In man the agonist and narcotic antagonist characteristics of buprenorphine have been demonstrated in opiate addicts. Thus oral buprenorphine in the dose range 6–16 mg has been shown to precipitate abstinence in highly dependent opiate addicts presenting for detoxification. On the other hand in a study involving subjects stabilised on a relatively low daily dose of oral methadone, sublingual buprenorphine could be substituted for methadone with only a low level of discomfort. In this situation buprenorphine was behaving as an opiate agonist of low intrinsic activity.

Thus buprenorphine has many of the desired characteristics of a treatment for opiate dependence (a) the ability to substitute for opiates in moderately dependent individuals (b) provide limited, long-lasting reinforcing (euphorigenic) effects which are acceptable to addicts (c) produce very mild abstinence effects when the drug is withdrawn, and (d) provide very good safety. With respect to (c) and (d) buprenorphine is markedly superior to methadone which is the only opioid agonist presently used for maintenance therapy.

For maintenance treatment there is the need for a product which can be safely administered on a "take home" basis. One of the potential problems of a sublingual buprenorphine product for the treatment of opiate addicts is its vulnerability to diversion if it is made available as a "take home" medication. Since the sublingual preparations to be absorbed have to be totally and relatively easily soluble, an addict in treatment could dissolve up the product and inject it. The useful sublingual dose range of buprenorphine for addict treatment (2 mg–8 mg) is about ten times higher than the analgesic dose range and when injected is potentially equivalent to 60–240 mg morphine or 30–120 mg heroin; as such it will have a significant value to street addicts. It is therefore to be expected that if such a sublingual buprenorphine product were made available as "take home" medication a proportion of it would fall into the hands of street opiate users. Injection of the diverted buprenorphine would negate the primary purpose of a treatment for opiate dependence—to prevent intravenous drug use which is a major source of AIDS infection.

Our U.S. Pat. No. 4,661,492 describes and claims in particular a method of treating pain which comprises the administration to a patient of a sublingually effective unit dosage of buprenorphine wherein the weight of buprenorphine is between about 0.1 to about 0.4 mg and simultaneously an amount of naltrexone sufficient to precipitate abstinence and thus prevent substitution in an opiate dependent subject, the weights of naltrexone and buprenorphine administered sublingually being within the ratio of 1:4 to 1:2. There is also disclosed and claimed an analgesic composition in sublingual unit dosage form comprising an active dose of buprenorphine of from about 0.1 to about 0.4 mg and an amount of naltrexone sufficient to prove aversive to a narcotic addict by parenteral administration but insufficient to compromise the analgesic action of the buprenorphine, the weight of naltrexone and buprenorphine being within the ratio of 1:4 to 1:2. The analgesic effect of these combination doses was equal to that of the equivalent dose of buprenorphine alone; however the ability of the combinations to precipitate abstinence in opiate-dependent subjects when injected was as great as that of the equivalent doses of naltrexone. Consequently an opiate dependent abuser would be discouraged from injecting the combination.

We have now found that there are doses of buprenorphine and naltrexone which when co-administered may be used in the treatment of opiate addicts.

According to this invention there is provided a pharmaceutical composition in sublingual unit dosage form for maintenance treatment of opiate addicts comprising from 2 to 8 mg buprenorphine and an amount of naltrexone sufficient to substantially attenuate the euphorigenic effect of the buprenorphine when injected and to provide greater opiate blocking effect than that of naltrexone alone wherein the weights of naltrexone and buprenorphine are within the ratio of 1:4 to 1:1. The preferred weight of buprenorphine is 4 mg and that of naltrexone is in the range of 1 to 4 mg.

In an aspect of the invention there is provided a pharmaceutical composition in sublingual unit dosage form for maintenance treatment of opiate addicts comprising from 2 to 8 mg buprenorphine and an amount of naltrexone sufficient to substantially attenuate the euphorigenic effect of the buprenorphine when injected and to provide greater opiate blocking effect than that of naltrexone alone wherein the amount of naltrexone is in the range of 2 to 8 mg. The preferred weight of buprenorphine is 4 mg and that of naltrexone is in the range of 2 to 4 mg.

It is to be understood that the use of the terms buprenorphine and naltrexone comprehend not only the bases but also their ph armaceutically acceptable salts. Particular preferred salts are the hydrochlorides.

The sublingual combinations of the present invention contain in unit doses greater amounts of naltrexone than the sublingual analgesic compositions of our earlier invention. This amount of naltrexone exerts a substantial opiate antagonist effect sublingually as well as when injected and in this respect the drug abuse treatment combinations differ from the analgesic combinations. The addiction treatment combinations will have substantially less reinforcing (euphorigenic) effect than buprenorphine alone particularly when injected and will not be attractive to any opiate abuser even those who are not physically dependent. They will also act sublingually in precipitating abstinence in dependent individuals. For this reason it is desirable that opiate addicts should first be stabilised on buprenorphine alone before transfer to the combination. This transfer can be made without a drug free period as is necessary in the present procedure for transferring addicts from opiates to oral naltrexone since there is no precipitated abstinence when buprenorphine-maintained subjects are treated with naltrexone.

Thus in another aspect of this invention there is provided a method of treating opiate dependent subjects in which addicts are treated by sublingual administration with a daily dose of 2 to 8 mg buprenorphine for 1 to 4 weeks followed by, as maintenance treatment, the daily simultaneous administration sublingually of 2 to 8 mg buprenorphine and an amount of naltrexone wherein the relative weights of naltrexone and buprenorphine are within the ratio of 1:4 to 1:1.

In a further aspect of this invention there is provided a method of treating opiate dependent subjects in which addicts are treated by sublingual administration with a daily dose of 2 to 8 mg buprenorphine for 1 to 4 weeks followed by, as maintenance treatment, the daily simultaneous administration sublingually of 2 to 8 mg buprenorphine and 2 to 8 mg naltrexone.

The preparations of the present invention are superior to equivalent preparations of buprenorphine alone for maintenance treatment of opiate dependence since they can be safely dispensed for "take home" use without fear of diversion. Furthermore we have shown that the abstinence effects following repeated administration of the combination are of an even lower level than those associated with buprenorphine alone.

The preparations of the present invention are superior to the present oral naltrexone maintenance product (a) based on their limited level of agonist effect which makes them more acceptable to addicts and therefore gives improved rates of retention in treatment.

(b) based on our finding that they have greater ability to block the acute effects of opiates. This is a most important factor determining the efficacy of a maintenance treatment for opiate dependence.

In the rat tail pressure test (Green and Young, Br. J. Pharmac., 6, p572, 1957), dose-response curves for morphine were determined after four days' pretreatment with twice-daily subcutaneous doses of saline, naltrexone (1 mg/kg) and buprenorphine/naltrexone (1 mg/kg+1 mg/kg). On day five, two hours after the last dose of the pretreatment drug, the dose-response curve for morphine was determined. Naltrexone shifted the morphine dose-response curve substantially to the right indicating blockade of opiate receptors whereas a combination of naltrexone (1 mg/kg) and buprenorphine (1 mg/kg) not only shifted the curve further to the right but also reduced the peak effect produced by morphine.

It is preferable to formulate the compositions in unit dosage forms ie physically discrete units containing the appropriate amounts of buprenorphine and naltrexone together with pharmaceutically acceptable diluents and/or carriers. Such compositions may be in the form of solid or liquid formulations.

Liquid preparations may be for example comprise buprenorphine or a non-toxic salt thereof plus naltrexone or a non-toxic salt thereof dissolved in 20–30% v/v aqueous ethanol buffered to between pH 4.5 to 5.5.

Compositions in the form of sublingual tablets contain soluble excipients such as lactose, mannitol, dextrose, sucrose or mixtures thereof. They will also contain granulating and disintegrating agents such as starch, binding agents such as povidone or hydroxypropyl-methyl cellulose and lubricating agents such as magnesium stearate.

The invention is illustrated by the following Examples:

EXAMPLE 1

10 ml of a sublingual solution containing 10 mg/ml buprenorphine and 10 mg/ml naltrexone in a pH5 mixture of a 30% v/v aqueous ethanol:citric acid/disodium hydrogen phosphate buffer was prepared as follows:

1. The buffer was prepared by mixing 3.8 ml 0.1M citric acid and 3.2 ml 0.2M disodium hydrogen phosphate.
2. 3.0 ml 95% v/v ethanol was added to the buffer increasing the pH from 4.6 to 5.0.
3. 108 mg buprenorphine hydrochloride was added with stirring until dissolved.
4. 110.7 mg naltrexone hydrochloride was added with stirring until dissolved.
5. Unit dose packs containing 0.2 ml were dispensed to give single doses of 2 mg buprenorphine and 2 mg naltrexone.

Unit dose packs containing 0.8 ml were dispensed to give single doses of 8 mg buprenorphine and 8 mg naltrexone.

EXAMPLE 2

A sublingual tablet having the following composition:

|  | mg/tablet |
| --- | --- |
| Buprenorphine HCl | 2.16 |
| Naltrexone HCl | 2.21 |
| Lactose | 26.98 |
| Mannitol | 18.0 |
| Maize starch | 9.0 |
| Povidone | 1.2 |
| Magnesium stearate | 0.45 |
|  | 60.0 | was prepared by screening all the materials with the exception of the magnesium stearate through a 750 μm sieve and blending them together. The mixed powders were then subjected to an aqueous granulation process and dried at 50° C. The resulting granules were forced through a 750 μm sieve and blended with magnesium stearate (pre-sieved through a 500 μm sieve). The tablet granules were compressed to yield tablets of 5.56 mm diameter and weight 60 mg.

EXAMPLE 3

The formulation of Example 2 was varied as follows, the method of manufacture being as for Example 2:

|  | mg/tablet |
|---|---|
| Buprenorphine HCl | 8.64 |
| Naltrexone HCl | 8.84 |
| Lactose | 45.22 |
| Mannitol | 36.0 |
| Maize starch | 18.0 |
| Povidone | 2.4 |
| Magnesium stearate | 0.90 |
|  | 120.0 |

In this Example the tablet granules were compressed to yield tablets of 7 mm diameter and weight 120 mg.

EXAMPLE 4

The formulation of Example 3 was varied as follows. The method of manufacture being as for Example 2.

|  | mg/tablet |
|---|---|
| Buprenorphine HCl | 4.32 |
| Naltrexone HCl | 4.42 |
| Lactose | 53.96 |
| Mannitol | 36.0 |
| Maize starch | 18.0 |
| Povidone | 2.4 |
| Magnesium stearate | 0.90 |
|  | 120.0 |

In this Example the tablet granules were compressed to yield tablets of 7 mm diameter and weight 120 mg.

We claim:

1. A method of treating opiate dependent subjects in which addicts are treated by sublingual administration with a daily dose of 2 to 8 mg buprenorphine for 1 to 4 weeks followed by, as maintenance treatment, the daily simultaneous administration sublingually of 2 to 8 mg buprenorphine and an amount of naltrexone wherein the weights of naltrexone and buprenorphine are within the ratio of 1:4 to 1:1.

2. A method of treating opiate dependent subjects in which addicts are treated by sublingual administration with a daily dose of 2 to 8 mg buprenorphine for 1 to 4 weeks followed by, as maintenance treatment, the daily simultaneous administration sublingually of 2 to 8 mg buprenorphine and 2 to 8mg naltrexone.

3. A pharmaceutical composition in sublingual unit dosage form for maintenance treatment of opiate addicts comprising from 2 to 8 mg buprenorphine and an amount of naltrexone sufficient to substantially attenuate the euphorigenic effect of the buprenorphine when injected and to provide greater opiate blocking effect than that of naltrexone alone wherein the weights of naltrexone and buprenorphine are within the ratio of 1:4 to 1:1.

4. A pharmaceutical composition in sublingual unit dosage form for maintenance treatment of opiate addicts comprising from 2 to 8 mg buprenorphine and an amount of naltrexone sufficient to substantially attenuate the euphorigenic effect of the buprenorphine when injected and to provide greater opiate blocking effect than that of naltrexone alone wherein the amount of naltrexone is in the range of 2 to 8 mg.

5. A pharmaceutical composition according to claim 3 wherein the weight of buprenorphine is 4 mg and that of naltrexone is in the range of 1 to 4 mg.

6. A pharmaceutical composition according to claim 3 wherein the weight of buprenorphine is 4 mg and that of naltrexone is in the range of 2 to 4 mg.

7. A pharmaceutical composition according to claim 4 wherein the weight of buprenorphine is 4 mg and that of naltrexone is in the range of 2 to 4 mg.

* * * * *